(12) United States Patent
Dransfeld et al.

(10) Patent No.: US 6,786,909 B1
(45) Date of Patent: Sep. 7, 2004

(54) IMPLANT FOR OSTEOSYNTHESES

(75) Inventors: Clemens Dransfeld, Niederlenz (CH); Fritz Magerl, St. Gallen (CH); Roger Roland Tognini, Widnau (CH); Thomas Andreas Peter, Holstein (CH)

(73) Assignee: Sepitec Foundation, Vaduz (LI)

( * ) Notice: Subject to any disclaimer, the term of this patent is extended or adjusted under 35 U.S.C. 154(b) by 0 days.

(21) Appl. No.: 10/111,224

(22) PCT Filed: Oct. 24, 2000

(86) PCT No.: PCT/EP00/10465

§ 371 (c)(1),
(2), (4) Date: Apr. 22, 2002

(87) PCT Pub. No.: WO01/30251

PCT Pub. Date: May 3, 2001

(30) Foreign Application Priority Data

Oct. 27, 1999 (DE) .......................... 199 51 760

(51) Int. Cl.[7] .......................... A61B 17/80; A61B 17/70
(52) U.S. Cl. .......................... 606/69; 606/61
(58) Field of Search .......................... 606/69, 70, 54, 606/59, 60, 61, 65, 66, 67, 71, 72, 73; 411/402–410

(56) References Cited

U.S. PATENT DOCUMENTS

| 4,219,015 | A | * | 8/1980 | Steinemann ................. 606/69 |
| 5,147,361 | A | | 9/1992 | Ojima et al. |
| 5,616,144 | A | * | 4/1997 | Yapp et al. ................... 606/69 |
| 5,647,712 | A | * | 7/1997 | Demirdogen et al. ....... 411/404 |
| 5,772,662 | A | * | 6/1998 | Chapman et al. ............. 606/69 |
| 6,206,881 | B1 | | 3/2001 | Frigg et al. |
| 6,454,769 | B2 | * | 9/2002 | Wagner et al. ................ 606/61 |

FOREIGN PATENT DOCUMENTS

| DE | 8628766.4 | 10/1996 |
| EP | 0206767 | 6/1998 |
| FR | 742618 | 12/1931 |
| WO | 8904150 | 3/1987 |
| WO | 9709000 | 12/1995 |
| WO | 0130251 | 10/2000 |

* cited by examiner

Primary Examiner—Cary E. O'Connor
Assistant Examiner—Candice C. Melson
(74) Attorney, Agent, or Firm—Volpe and Koenig, P.C.

(57) ABSTRACT

An implant for osteosyntheses including a plate with a plurality of holes following in succession in the longitudinal direction whereby at least most of the holes intended to receive the screws are offset in alternation generally away from a center plane whereby a center axis of each of the holes forms an acute angle with the center plane of the plate.

23 Claims, 2 Drawing Sheets

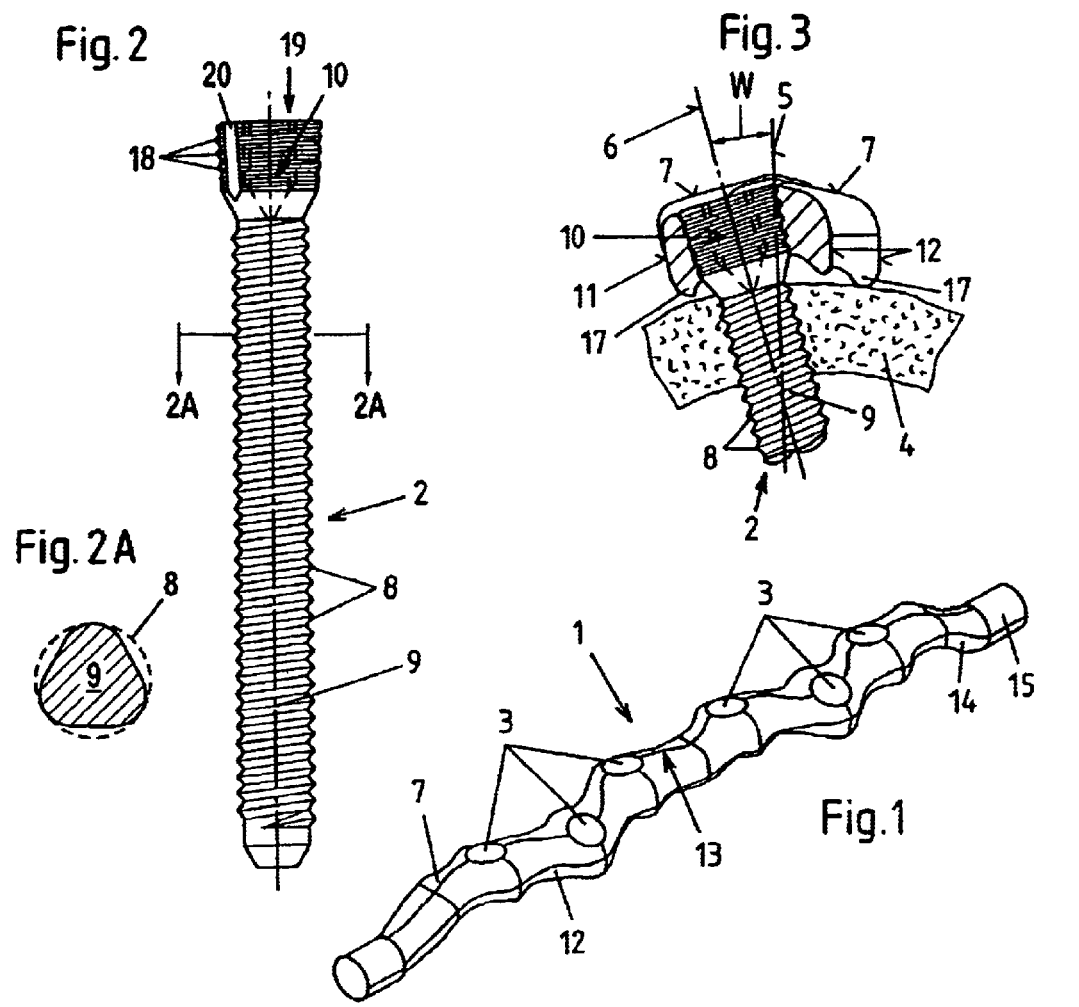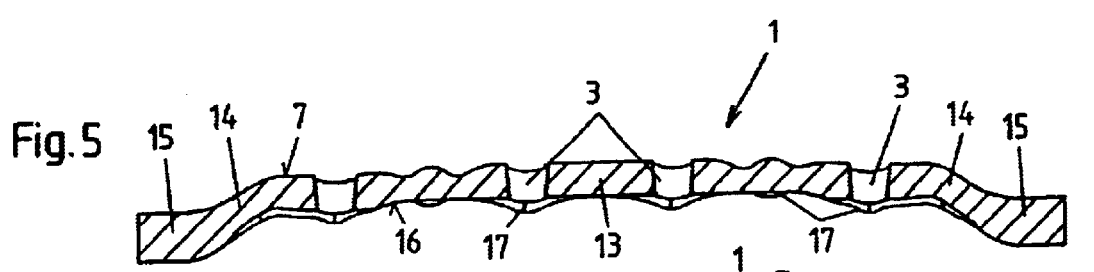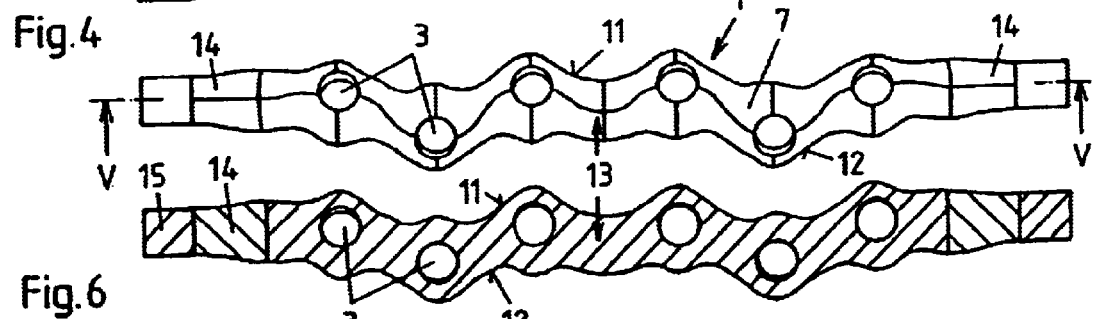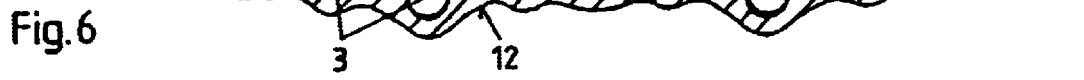

IMPLANT FOR OSTEOSYNTHESES

BACKGROUND OF THE INVENTION

This invention relates to an implant for osteosyntheses consisting of a plate provided with a plurality of holes following in succession in the longitudinal direction and screws that can be inserted through the holes in the plate and can be screwed into a bone in the proper position, whereby at least most of the holes intended to receive the screws are offset in alternation toward the outside, based on an imaginary center plane of the plate, whereby the center axes of the holes form an acute angle with the imaginary center plane of the plate and whereby the holes taper from the surface of the plate which is intended to face outward.

In the case of a known bone plate (German Utility Model 86 28 766), holes that are offset laterally with respect to the central longitudinal axis are provided so that screws can be inserted into them. If the holes are offset by a larger angular amount of 10° to 20° (based on the round bone cross section) from the center axis, the plate is curved about an axis parallel to the longitudinal direction to adapt it to the bone surface or it otherwise approximates a cylindrical shape (in particular with a polygonal cross section). Due to the fact that the transverse dimension of the bone plate need not be broadened significantly, despite the laterally offset arrangement of the holes, considered locally, the plate can be deformed with the usual tools and adapted individually to the shape of the bone. The width of the plate corresponds approximately to the width of a normal narrow plate, but the course of this plate has a zigzag character due to the recesses. Thus, this plate may also have a helical twist, so that the optimal fastening points can be achieved in this case, depending on the type of fracture. Since the state-of-the-art plates are relatively broad an thus it is difficult to adapt them to the respective fracture situations, the goal is to design the known bone plate so that it can be adapted to a larger number of types of fractures due to the individual shaping.

In addition, a bone plate has become known (European Patent Application 0 206 767) in which the holes are arranged offset laterally with respect to the central longitudinal axis, the holes being countersunk essentially in the form of a section of a sphere, and the underside of the head of the screws having a corresponding cross-sectional shape. Therefore, the screw head can always sit snugly in the countersunk depression in the bone plate. However, a position between the bone plate and screw that has angular stability cannot be achieved in this way.

In the case of another known bone plate (International Patent Application WO-97/09000), holes with a conical taper are provided and heads with a corresponding shape are also provided on the screws to be used, but no permanent connection with angular stability can be achieved with screws running with parallel axes. In this case a large portion of the forces must thus be transmitted from the plate to the bone surface through direct contact pressure.

In the case of the mechanical principle of conventional plate osteosynthesis used in the past, the plate is in direct contact with the bone either over the surface or with projecting strips or cams. Therefore, the contact pressure of the plate on the bone and the resulting friction of the plate against the bone is the deciding factor for the transmission of forces from one bone fragment to the other. This therefore results in a direct transmission of forces from the bone to the plate and from the plate back to the bone. As soon as a screw that has been inserted becomes loosened, i.e., is slightly unscrewed, this stabilization principle fails. However, there are also problems here from a biological standpoint. A zone of necrosis develops beneath the plate due to poor circulation. The vessels of the periosteum are clamped off.

BRIEF DESCRIPTION OF THE INVENTION

The object of the present invention is to create an implant of the type defined preamble with which the transmission of force over a plate can be improved significantly from both a mechanical and a biological standpoint.

This is accomplished according to this invention by the fact that the holes in the plate have a conical taper and the screws have a head which has a conical taper toward the shaft which is provided with a thread, so that the conical taper essentially corresponds to that of the sections formed by the holes, and the head can be secured in the holes in a friction-locked and/or form-fitting manner; the plate is designed with multiple twists as seen in its longitudinal direction, whereby the main alignment across the longitudinal extent of the plate in the area of the individual holes runs at a right angle to the center axis of the corresponding hole, and the plate is designed with a slight curvature, as seen from the side, whereby a tendon passed through the ends of the plate is at a distance from a center section of the plate.

These measures achieve the result that the plate is no longer in contact with the bone under pressure. There is actually a gap between the bone and the plate. The transfer of forces from one fragment to the other then takes place as follows: bone—screw shaft—head of the screw(s)—plate—head of the screw(s)—screw shaft—bone. The prerequisite for this was the possibility created by this invention, namely that there would be a clamping connection between the head of the screws and the plate having angular stability. Due to the clamping connection of the head of the screw in the corresponding hole in the plate at a stable angle, an optimal angular stability and protection against unscrewing are created. Such protection against unscrewing is especially advantageous because unscrewing of the screws might occur merely due to repetitive alternating loads.

In addition to a secure stabilization, it is thus optionally also possible to use fewer screws. Circulation disorders do not occur at all beneath the plate or they occur only to a much lesser extent, because the vessels of the periosteum are not clamped off.

The boreholes in the bones for inserting screws are not all aligned in one row. Therefore, splitting off of fragments is essentially prevented, and in addition, this also greatly reduces circulation disorders. The convergence of the screws inserted has an especially good effect. Screws inserted successively into a bone thus approximately intersect at the center of the medullary space of the bone. This measure greatly increases the torsional stability of the plate osteosynthesis. Screws implanted in a line relatively close together may cause the bone to fracture when exposed to strong torsional forces. Screws implanted in a line relatively close together are also more likely to cause circulation disorders, which have a negative effect due to the interruption in the blood vessels running in the longitudinal Haversian channels in comparison with holes arranged at an offset and thus in comparison with screws intersecting one another sequentially.

Due to the measures according to this invention, a step toward an elastic plate has been achieved, whereby natural bone healing with the development of callous is expected, as was previously the case when using a plaster cast, due to the possibilities of movement.

Due to the fact that the plate is designed with multiple twists, as seen in its longitudinal direction, the main alignment across the longitudinal extent of the plate running at least approximately at a right angle to the center axis of the corresponding hole in the area of the individual holes. Therefore, the plate is approximately parallel to the surface of the bone in the respective area of attachment. Thus, there is always essentially a uniform gap between bone and plate.

It is also proposed here that the lateral limits on the plate should follow essentially the offset holes and the exterior contours of the holes, so that the plate has essentially a wavy course over the length as seen from above. This permits an at least approximately uniform stability over the length of the plate despite the fact that the plate is manufactured by saving on material. Thus this guarantees that the plate used will not be overdimensioned.

To permit an accurate alignment especially in the transitional area between two bone fragments that are to be joined together, it is proposed that the two holes next to the center section of the plate should be facing the same side limit of the plate.

In this connection, it is also advantageous if the imaginary center plane of the plate is also the center plane of the center section of the plate. This facilitates centering of the plate on the bone.

An optimal structural design is obtained by the fact that the size of the cross-sectional area of the plate is at least approximately constant over its entire length. This does not result in any weak points caused by the holes in the plate.

Especially in the connecting area between two bones, i.e., in the area bridging a bone fracture, for example, special forces are to be transmitted by the plate, but it is advantageous if the cross-sectional area of the plate is designed to be larger in the center section than in the other sections of the plate.

To be able to introduce the forces through the screws into each bone fragment to an equal extent, it is proposed that the distance between the holes, as seen in the longitudinal direction of the plate from the ends of the plate should be the same, but that the distance between the two holes adjacent to the center section should be greater. Due to the greater distance of the two screws near the fracture from the fracture surface, circulation disorders are prevented. In the bone, the main blood vessels run in the longitudinal direction. Thus, if the screw holes near the fracture are too close to the fracture surface they may result in a "shadow" circulation disorder.

In addition, it is also proposed that cams projecting on one or both sides of each hole close to the side borders should be formed on the underside of the plate. These cams prevent the plate from being in full surface contact with the bone, and they may optionally increase the torsional stability and relieve the screw necks at the transition between the screw shaft and the head. These cams alone do not significantly interfere with circulation in the bone. The locking effect of the screws in the plate itself achieves the result that the plate ultimately remains a certain distance away from the surface of the bone.

To prevent tissue damage to soft tissue, especially at the tendons which lie above the plate or which are pulled over the plate, it is proposed that the two ends and the edges and transitions of the plate should be designed to be flat and rounded.

According to another special embodiment, the center axes of the holes form an acute angle of 15° with the imaginary center plane of the plate. Due to the acute angle at which the screws are screwed in and the intersecting holes together with screws, the torsional stability of the osteosynthesis is significantly improved. The screws are under bending stress to a much lower extent.

In addition, it is proposed according to this invention that the plate shall be manufactured from fiber-reinforced thermoplastics and the anisotropy of the elastic properties of the plate shall be adjusted to the elasticity or rigidity of the bone. The osteosynthesis plate system according to this invention is thus designed as elastic fixation. Thus, a homoelasticity is achieved, because the plate has only a similar rigidity and not an equivalent rigidity, as required of isoelastic implants. Due to the use of such a material and the corresponding manufacture, this yields the important advantage of a more elastic osteosynthesis. This results in less stress shielding and less reactive osteoporosis. In addition, the development of callus is stimulated. Especially due to the combination of a plate of fiber-reinforced thermoplastics and locking between the head of the screw and the wall of the hole in the plate, an elastic plate for optimal natural bone healing is achieved.

In this connection, it is especially advantageous that the anisotropy of the elastic properties of the plate is adjustable according to the formula: E modulus (longitudinal): E modulus (tangential)=0.3 to 0.7. The E modulus of such a homoelastic plate varies between 30 and 70 GPa (in the case of bone, this is up to 20 GPa). A ratio of approximately 0.3 was obtained according to this formula for an evaluation plate. This ratio with the evaluation plate was even lower in the case of the system, i.e., when mounted on a bone substitute. The offset screws bring this ratio to a good average of approx. 0.5. Fine adjustment of these anisotropic elastic properties can be accomplished through appropriate control in the manufacturing process, e.g., in a reciprocal extrusion process.

Another advantageous measure is seen as the fact that the head of the screw is provided with a thread. Preferably the head of the screw is provided with a fine thread. This permits an optimal initial stress of the screw in the plate. The osteosynthesis plates used today are under initial stress with respect to the bone. The stresses thus induced in the bone may lead to absorption and degradation of bone and thus to weakening of the bone, which in turn increases the risk of a refracture after removing the implant. Thanks to the initial stress of the screws in the plate itself, no pressure burden is induced from the plate into the bone, so this promises a greater success in healing.

Due to the use of a thread, preferably an optionally double fine thread, an optimal locking effect of the head of the screw in the corresponding hole in the plate is achieved. Due to the slightly conical head having a fine thread, insertion of the screw head into the corresponding hole in the plate is facilitated on the one hand, which could be important in the case of a slightly eccentric bore of the screw channel in the bone, while on the other hand, this yields and effective locking of the head in the corresponding hole.

Due to the use of a thread, especially a fine thread, on the head of the screw, good protection against loosening or ejection of the head out of the hole is also created. Such axial forces occur when a force acts from the bone against the head of the screw in the longitudinal axis of the screw, e.g., a torsional or bending stress.

An advantageous measure is also the fact that the head of the screw is provided with one or more longitudinal groove(s) in the area of the thread. This creates the possibility of accommodating tissue debris.

For additional locking protection of the screw, it is provided that the screw which has been provided with a thread on its shaft shall be designed with an out-of-round cross section, e.g., trilobular. After screwing in the screw, the bone tissue that grows back provides a natural protection, so to speak, because the out-of-round screw is clamped.

To permit the great torque to be transmitted to the best extent possible when screwing in the screws, but also when unscrewing them, it is proposed that the head of the screw shall be provided with an internal point of action for a tool with four curved projections extending radially outward from a central opening.

BRIEF DESCRIPTION OF THE SEVERAL VIEWS OF THE DRAWINGS

Additional features and special advantages of this invention are explained in greater detail in the following description on the basis of the drawings, which show:

FIG. 1: an inclined view of a plate that can be used as an implant for an osteosynthesis;

FIG. 2 a view of a screw that can be used as an implant for an osteosynthesis;

FIG. 2A is a cross-sectional view of the shaft of FIG. 2 as taken along the line 2A—2A of FIG. 2 illustrating the out-of-round cross-section which may be preferably, but not necessarily, trilobular;

FIG. 3 a section through an example of use of the implant of plate and screw on a bone;

FIG. 4 a top view of a plate;

FIG. 5 a section according to line V—V in FIG. 4;

FIG. 6 a horizontal section according to line VI—VI in FIG. 7;

DETAILED DESCRIPTION OF THE INVENTION

Figure 7:
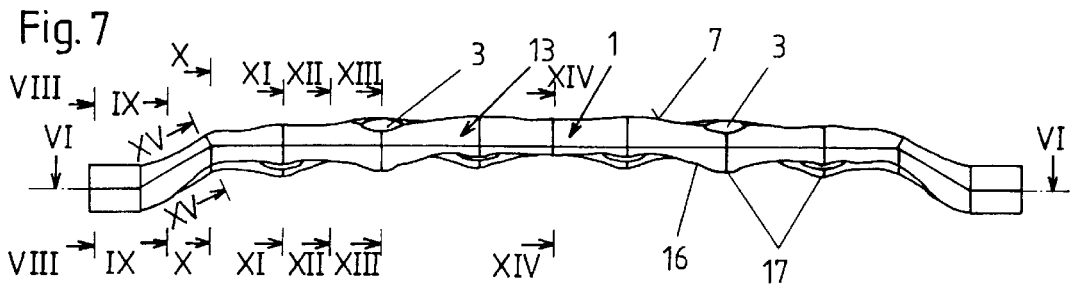
FIG. 7 a side view of the plate.

The implant for osteosyntheses illustrated in the drawings consists of a plate 1 provided with several holes 3 following in succession in the longitudinal direction plus in most cases several screws 2 which can be inserted through the holes 3 in the plate 1 and can be screwed into a bone 4 in the proper position. At least most of the holes 3 intended to receive the screws 2 are arranged with an offset to the outside in alternation, based on an imaginary center plane 5 of the plate 1. The center axes 6 of the holes 3 form an acute angle W with the imaginary center plane 5 of the plate 1. The holes 3 taper conically starting from the surface 7 of the plate 1 which is intended to lie on the outside. The screws 2 have a head 10 which tapers conically toward the shaft 9 which is provided with a thread 8, essentially corresponding to the sections formed by the holes 3. The screw 2 can be secured in the holes 3 by its head 10 in a friction-locked and/or form-fitting manner.

The side borders 11, 12 of the plate 1 follow essentially the offset holes 3 and also the outside contours of the holes 3. The plate 1 therefore has an essentially wavy course over its length as seen in a top view. Furthermore, the plate 1 is designed with multiple twists, as seen in its longitudinal direction, with the main alignment across the longitudinal extent of the plate running at least approximately at a right angle to the center axis 6 of the corresponding hole 3 in the area of the individual holes 3.

The two holes 3 closest to the center section 13 of the plate, based on their length, are facing the same side borders 11 (or 12) of the plate 1. This center section 13 need not always be arranged exactly in the center, based on the length of the plate 1. In the case of plates having an even number of holes 3, it will probably always be the center (except in the case of extremely long plates). When there is an uneven number of holes 3, the center section 13 is between the holes x/2+0.5 and x/2−0.5. The construction here is advantageously such that the imaginary center plane 5 of the plate 1 is also the center plane 5 of the center section 13 of the plate 1.

When seen from the side, the plate 1 is designed with a slight curvature, whereby the distance of a tendon passing through the ends 14 of the plate to the center section 13 may amount to approximately 2 mm, for example. This longitudinal bending can also counteract the bowing of a fracture when a bending moment acts perpendicularly on the underside of the plate. Due to this longitudinal bending, a better adaptation to the geometry of the bone of the forearm has become made possible.

The size of the cross-sectional area of the plate 1 is at least approximately constant over its entire length. However, the cross-sectional area of the plate 1 in the area of the center section 13 may be designed to be larger than in the other sections of the plate 1. Thus, an additional optimization of the torsional stability is possible precisely in this center section which extends over the fracture area.

The distance between the holes 3 as seen in the longitudinal direction of the plate 1, starting from the ends 14 of the plate is uniform. However, the distance between the two holes 3 adjacent to the center section 13 may be greater. Depending on the area of use or special circumstances, it is also conceivable to design the hole spacings to be variable.

On the underside 16 of the plate 1, cams 17 which project outward on one or both sides of each hole 3 may be provided close to the side borders 11, 12. These cams 17 may be advantageous in installing the plate, to thereby produce a suitable gap between the surface of the bone and the plate 1. In the final state, however, the plate 1 is not pressed against the surface of the bone 4, so that the cams rest on the surface without any pressure and practically only secure the distance in installation themselves. Due to screwing in the screws themselves, there is by no means any pressure of the plate against the surface of the bone.

The two ends 14 of the plate 1, as well as all edges and transitions, are designed to be flat and rounded. The shoulders 15 which fare shown as approximately cylindrical in the figure are sections that are attached only for manufacturing reasons, but as a rule they are removed before the final implantation.

To achieve an optimal convergence of the screws 2 which are to be screwed in (see also the diagram in FIG. 3), the center axes 6 of the holes 3 are aligned in an acute angle W to the imaginary center plane 5 of the plate 1, and thus when the screws 2 are screwed in, their center axes are also so aligned. The center axes 6 of the holes 3 form an acute angle W of approximately 15° with the imaginary center plane 5 of the plate 1 to advantage.

The plate 1 and the screw 2 as well are made of fiber-reinforced thermoplastics to advantage. They may be manufactured in a molding process, such as an extrusion process or in a reciprocal extrusion process. The anisotropy of the elastic properties of the plate 1 is adjustable to the elasticity or rigidity of the bone 4. In manufacture of the plate, the anisotropy of the elastic properties is adjustable according to the formula: E modulus (longitudinal): E modulus (tangential)=0.3 to 0.7. An average of 0.5 is regarded as optimal.

In order to achieve a proper locking effect of the head 10 of the screw 2 in the corresponding hole 3 in the plate 1, i.e., to achieve the required rigidity of this connection, the head 10 of the screw 2 is advantageously provided with a thread 18. A fine thread is provided in an optimal manner on the head 10 of the screw which is designed with a conical taper in a corresponding construction with the hole 3. In the case of a dual-thread embodiment of the fine thread, a thread pitch which is adapted to the thread 8 on the shaft 9 is achieved, and in addition, a fixed locking effect of the head 10 of the screw 2 with respect to the plate 1 is also obtained. If in addition the head 10 of the screw 2 is also provided with one or more longitudinal groove(s) 20 in the area of the thread 18, this creates a possibility for accommodating tissue debris. When the screw 2 is screwed in, suddenly an increase in torque is achieved in the last couple of revolutions, whereby this higher torque comes about due to the mutual engagement of the wall of the hole 3 and the head 10 of the screw 2. This means an optimal locking effect between the screw 2 and the plate 1, so there can never be any stripping of the thread 8 in the bone 4.

To achieve another possibility of locking the screw, the screw 2 is designed with an out-of-round cross section, e.g., trilobular, on its shaft 9 which is provided with a thread 8. Such cross-sectional shapes are usually referred to as being "orbiform." Within the scope of this invention, it would also be conceivable to design the area of the head 10 of the screw 2 with an out-of-round cross section.

The head 10 of the screw 2 is provided with an internal tool action point 19, which is advantageous for installing and also removing such screws. An advantageous embodiment would provide for an internal tool acting point 19 with four curved projections extending radially outward from a central opening. In this way, a very advantageous transfer of torque is possible.

Figure 8:
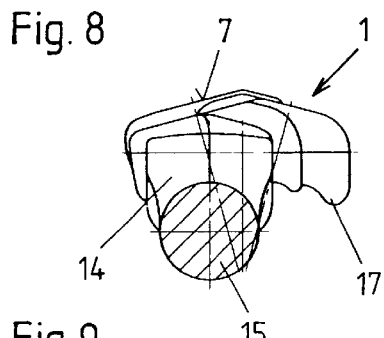
FIGS. 8 through 15 sections according to lines VIII—VIII through XV—XV in FIG. 7.
Figure 9:
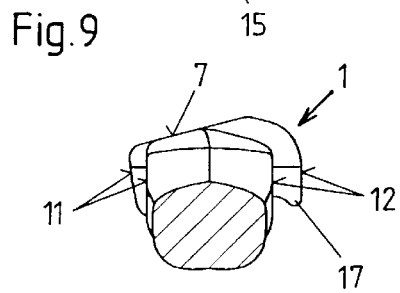
Figure 10:
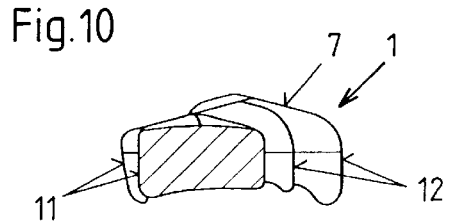
Figure 15:
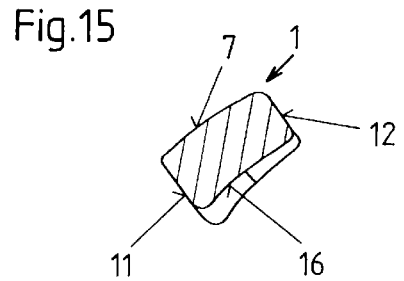
Figure 11:
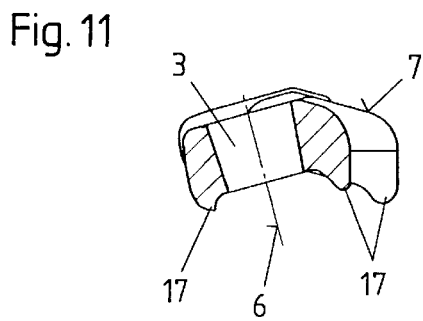
Figure 12:
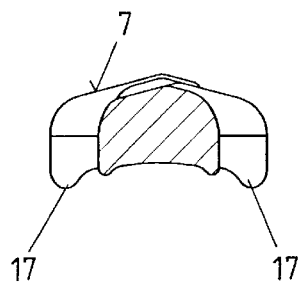
Figure 13:
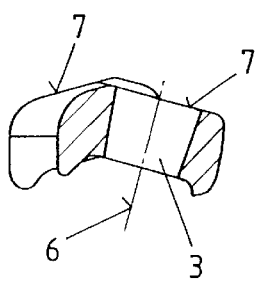
Figure 14:
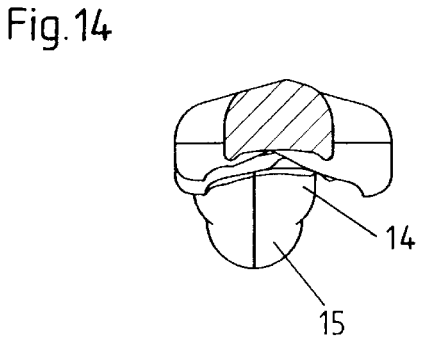

The sectional diagrams in FIGS. 8 through 15 do not require any further explanation. The technical details are already apparent from the preceding description, and the sectional diagram speaks for itself.

Essential inventive features are embodied in both the plate 1 and in the screw 2, additionally entailing ion their totality an optimal increase in the suitability of implants.

What is claimed is:

1. An implant for osteosyntheses, comprising:
   a plate (1) provided with a surface defining a plurality of holes (3) and two ends, the plate defining a longitudinal direction and a center plane disposed generally parallel to the longitudinal direction and located generally perpendicular to the surface, the holes generally following one another in the longitudinal direction and being positioned outwardly offset from the center plane with at least most of the holes being offset outwardly from the center plane in a direction generally opposite from neighboring holes, the holes each having a center axis (6) forming an acute angle (W) with the center plane (5) of the plate (1) such that, when inserted, the screws are not all aligned in parallel, each of the holes (3) generally tapering inwardly from the surface (7) to form a conical taper; the screws (2) each having a head (10) which tapers in a conical shape toward a shaft (9) and adapted to be secured in the holes (3) in a friction-locked and/or form-fitting manner; the plate (1) being configured to have multiple twists as seen in its longitudinal direction, whereby in the area of the individual holes (3) the main alignment across the longitudinal extent of the plate (1) runs at a right angle to the center axis (6) of the corresponding hole (3) and the plate (1) has a slight curvature along the longitudinal direction, whereby a tendon placed through the two ends (14) of the plate (1) is at a distance from a center section (13) of the plate (1).

2. The implant according to claim 1, wherein the plate (1) further comprises a length and two side borders (11, 12) generally follow an outside contour of the so that the plate (1) has an essentially wavy course over the length, as viewed along the center plane.

3. The implant according to claim 1, wherein the center plane (5) of the plate (1) is centrally aligned with the center section (13) of the plate (1).

4. The implant according to claim 1, wherein a cross-sectional area of the plate (1), not including the area occupied by the holes, as taken generally perpendicularly to the longitudinal axis, is approximately constant over an entire length of the plate.

5. The implant according to claim 1, wherein the cross-sectional area of the plate (1), as measured generally perpendicularly to the longitudinal axis, is designed to be greater in the area of the center section (13) than in the other sections of the plate (1).

6. The implant according to claim 1, wherein a cam (17) projecting outward on one or both sides of each hole (3) is provided near two side borders (11, 12) on an underside (16) of the plate (1).

7. The implant according to claim 1, wherein the two ends (14) and a plurality of edges and transitions of the plate (1) are designed to be flat and rounded.

8. The implant according to claim 1, wherein the head (10) of the screw (2) is provided with an internal tool engagement point (19) with four curved projections extending radically outward from a central opening.

9. The implant according to claim 1, wherein two of the holes (3) closest to the center section (13) of the plate (1) are offset from the center plane in the same direction.

10. The implant according to claim 9, wherein a distance between the holes (3) in the longitudinal direction of the plate (1), as seen along the center plane, is the same except for the two holes (3) adjacent to the center section (13) which are further spaced apart.

11. The implant according to claim 1, wherein the head (10) of the screw (2) is provided with a thread (18).

12. The implant according to claim 11, wherein the head (10) of the screw (2) is provided with one or more longitudinal groove(s) proximate to the thread (18).

13. An implant for osteosyntheses, comprising:
    a plate provided with a surface defining a plurality of holes, the plate defining a longitudinal direction and a center plane disposed generally parallel to the longitudinal direction and located generally perpendicular to tile surface, the plurality of holes generally following one another in the longitudinal direction and being positioned outwardly offset from the center plane with at least most of the plurality of holes being offset outwardly from the center plane in a direction generally opposite from neighboring holes, the plurality of holes each having a center axis forming an acute angle (W) with the center plane of the plate.

14. The implant of claim 13, wherein the plate has a slight curvature, as viewed from a side, whereby a tendon placed through an end of the plate is spaced from a center section of the plate.

15. The implant of claim 13, wherein a cross-sectional area of the plate, not including the area occupied by the holes, as taken generally perpendicularly to the longitudinal axis, is generally constant throughout the plate.

16. The implant of claim 13, wherein the center axis of each of the plurality of holes forms an acute angle of approximately fifteen (15°) degrees with the center plane of the plate.

17. The implant of claim 13, wherein the plate is manufactured from fiber-reinforced thermoplastics, and the anisotropy of the elastic properties of the plate is adjusted to the elasticity or rigidity of the bone.

18. The implant of claim 13, wherein the plurality of screws tend to converge when engaged with the plate due to the acute angle between the center as of each of the plurality of holes and the center plane.

19. The implant according to claim 13, wherein the out-of-round cross section is trilobular.

20. An implant for osteosyntheses, comprising:
a plate (1) provided with a surface defining a plurality of holes (3) and two ends, the plate defining a longitudinal direction and a center plane disposed generally parallel to the longitudinal direction and located generally perpendicular to the surface, the holes generally following one another in the longitudinal direction and being positioned outwardly offset from the center plane with at least most of the holes being offset outwardly from the center plane in a direction generally opposite from neighboring holes, the holes each having a center axis (6) forming an acute angle (W) with the center plane (5) of the plate (1) such that, when inserted, the screws are not all aligned in parallel, the holes (3) each generally tapering inwardly from the surface (7) to form a conical taper; the screws (2) each having a head (10) which tapers in a conical shape toward a shaft (9) and adapted to be secured in the holes (3) in a friction-locked and/or form-fitting manner; the plate (1) being configured to have multiple twists as seen in its longitudinal direction, whereby in the area of the individual holes (3) the main alignment across the longitudinal extent of the plate (1) runs at a right angle to the center axis (6) of the corresponding hole (3) and the plate (1) has a slight curvature along the longitudinal direction, whereby a tendon placed through the two ends (14) of the plate (1) is at a distance from a center section (13) of the plate (1), wherein the center axis (6) of each of the holes (3) forms an acute angle (W) of approximately fifteen (15°) degrees with the center plane (5) of the plate (1).

21. An implant for osteosyntheses, comprising:
a plate (1) provided with a surface defining a plurality of holes (3) and two ends, the plate defines a longitudinal direction and a center plane disposed generally parallel to the longitudinal direction and located generally perpendicular to the surface, the holes generally following one another in the longitudinal direction and being positioned outwardly offset from the center plane with at least most of the holes being offset outwardly from the center plane in a direction generally opposite from neighboring holes, the holes each having a center axis (6) forming an acute angle (W) with the center plane (5) of the plate (1) such that, when inserted, the screws are not all aligned in parallel, the holes (3) each generally tapering inwardly from the surface (7) to form a conical taper; the screws (2) each having a head (10) which tapers in a conical shape toward a shaft (9) and adapted to be secured in the holes (3) in a friction-locked and/or form-fitting manner; the plate (1) being configured to have multiple twists as seen in its longitudinal direction, whereby in the area of the individual holes (3) the main alignment across the longitudinal extent of the plate (1) runs at a right angle to the center axis (6) of the corresponding hole (3) and the plate (1) has a slight curvature along the longitudinal direction, whereby a tendon placed through the two ends (14) of the plate (1) is at a distance from a center section (13) of the plate (1), wherein the plate (1) is manufactured from fiber-reinforced thermoplastics, and the anisotropy of the elastic properties of the plate (1) is adjusted to the elasticity or rigidity of the bone (4).

22. An implant for osteosyntheses, comprising:
a plate (1) provided with a surface defining a plurality of holes (3) and two ends, the plate defines a longitudinal direction and a center plane disposed generally parallel to the longitudinal direction and located generally perpendicular to the surface, the holes generally following one another in the longitudinal direction and are positioned outwardly offset from the center plane with at least most of the holes being offset outwardly from the center plane in a direction generally opposite from neighboring holes, the holes each having a center axis (6) forming an acute angle (W) with the center plane (5) of the plate (1) such that, when inserted, the screws being not all aligned in parallel, each of the holes (3) generally tapering inwardly from the surface (7) to form a conical taper; the screws (2) each having a head (10) which tapers in a conical shape toward a shaft (9) and adapted to be secured in the holes (3) in a friction-locked and/or form-fitting manner; the plate (1) being configured to have multiple twists as seen in its longitudinal direction, whereby in the area of the individual holes (3) the main alignment across the longitudinal extent of the plate (1) runs at a right angle to the center axis (6) of the corresponding hole (3) and the plate (1) has a slight curvature along the longitudinal direction, whereby a tendon placed through the two ends (14) of the plate (1) is at a distance from a center section (13) of the plate (1), wherein the anisotropy of the elastic properties of the plate (1) is adjustable according to the formula: E modulus (longitudinal): E modulus (tangential)=0.3 to 0.7.

23. An implant for osteosyntheses, comprising:
a plate (1) provided with a surface defining a plurality of holes (3) and two ends, the plate defines a longitudinal direction and a center plane disposed generally parallel to the longitudinal direction and located generally perpendicular to the surface, the holes generally following one another in the longitudinal direction and are positioned outwardly offset from the center plane with at least most of the holes being offset outwardly from the center plane in a direction generally opposite from neighboring holes, the holes each having a center axis (6) forming an acute angle (W) with the center plane (5) of the plate (1) such that, when inserted, the screws are not all aligned in parallel, the holes (3) each generally taper inwardly from the surface (7) to form a conical taper; the screws (2) each have a head (10) which tapers in a conical shape toward a shaft (9) and can be secured in the holes (3) in a friction-locked and/or form-fitting manner; the plate (1) being configured to have multiple twists as seen in its longitudinal direction, whereby in the area of the individual holes (3) the main alignment across the longitudinal extent of the plate (1) runs at a right angle to the center axis (6) of the corresponding hole (3) and the plate (1) has a slight curvature along the longitudinal direction, whereby a tendon placed through the two ends (14) of the plate (1) is at a distance from a center section (13) of the plate (1), wherein the shaft (9) of the screw (2) has an out-of-round cross section, as taken generally perpendicularly to a longitudinal axis of the shaft (9), at least one thread (8) being located generally around the shaft.

* * * * *